United States Patent
Shu

(10) Patent No.: US 11,866,516 B2
(45) Date of Patent: *Jan. 9, 2024

(54) ISOLATED PEPTIDE, ANTI-CANCER MEDICINAL COMPOSITION INCLUDING THE SAME AND METHOD OF SPECIFICALLY REDUCING OR INHIBITING ACTIVITIES OF CANCER CELLS USING THE SAME

(71) Applicant: National Sun Yat-Sen Univesity, Kaohsiung (TW)

(72) Inventor: Chih-Wen Shu, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/841,929

(22) Filed: Jun. 16, 2022

(65) Prior Publication Data
US 2022/0340618 A1 Oct. 27, 2022

Related U.S. Application Data

(63) Continuation of application No. 17/096,463, filed on Nov. 12, 2020, now Pat. No. 11,396,529.

(51) Int. Cl.
| C07K 14/005 | (2006.01) |
| C07K 7/06 | (2006.01) |
| A61P 35/00 | (2006.01) |
| A61K 38/00 | (2006.01) |

(52) U.S. Cl.
CPC .............. *C07K 7/06* (2013.01); *A61K 38/00* (2013.01); *A61P 35/00* (2018.01); *C07K 14/005* (2013.01); *C07K 2319/70* (2013.01)

(58) Field of Classification Search
None
See application file for complete search history.

(56) References Cited

U.S. PATENT DOCUMENTS 11,396,529 B2 * 7/2022 Shu .................. A61K 38/00
2005/0097640 A1 5/2005 Fernandes

FOREIGN PATENT DOCUMENTS

| CN | 102659951 A | 9/2012 |
| EP | 2354155 A2 | 8/2011 |

OTHER PUBLICATIONS

Ivan Dikic et al., "Mechanism and medical implications of mammalian autophagy," Nature Reviews Molecular Cell Biology, Jun. 2018, pp. 349-364, vol. 19.

Noboru Mizushima et al., "Autophagy fights disease through cellular self-digestion," Nature, Feb. 28, 2008, pp. 1069-1075, vol. 451(7182).
Pei-Feng Liu et al., "ATG4B promotes colorectal cancer growth independent of autophagic flux," Autophagy, Aug. 1, 2014, pp. 1454-1465, vol. 10, Issue 8.
Pei-Feng Liu et al., "Association of ATG4B and Phosphorylated ATG4B Proteins with Tumorigenesis and Prognosis in Oral Squamous Cell Carcinoma," Cancers, Nov. 23, 2019, pp. 1-23, vol. 11(12):1854.
Katharina Rothe et al., "The core autophagy protein ATG4B is a potential biomarker and therapeutic target in CML stem/progenitor cells," Blood, Jun. 5, 2014, pp. 3622-3634, vol. 123, No. 23.
Tatsuro Maruyama et al., "Autophagy-regulating protease Atg4: structure, function, regulation and inhibition," The Journal of Antibiotics, Sep. 13, 2017, pp. 72-78, vol. 71.
Debra Akin et al., "A novel ATG4B antagonist inhibits autophagy and has a negative impact on osteosarcoma tumors," Autophagy, Oct. 30, 2014, pp. 2021-2035, vol. 10, Issue 11.
Pei-Feng Liu et al., "Ablation of ATG4B Suppressed Autophagy and Activated AMPK for Cell Cycle Arrest in Cancer Cells," Cellular Physiology and Biochemistry, Nov. 23, 2017, pp. 728-740, vol. 44.
Jin-Ju Mao et al., "Nucleotide variation in ATG4A and susceptibility to cervical cancer in Southwestern Chinese women," Oncology Letters, Dec. 20, 2017, pp. 2992-3000, vol. 15.
Jonas Wolf et al., "A mammosphere formation RNAi screen reveals that ATG4A promotes a breast cancer stem-like phenotype," Breast Cancer Research, Nov. 14, 2013, pp. 1-13, vol. 15:R109.
Martina Antonelli et al., "ATM kinase sustains breast cancer stem-like cells by promoting ATG4C expression and autophagy," Oncotarget, Feb. 20, 2017, pp. 21692-21709, vol. 8, No. 13.
R. Read et al., "Histopathological and Neurological Features of Atg4b Knockout Mice," Veterinary Pathology, Jul. 15, 2010, pp. 486-494, vol. 48(2).
Guillermo Marino et al., "Autophagy is essential for mouse sense of balance," The Journal of Clinical Investigation, Jul. 1, 2010, pp. 2331-2344, vol. 120, No. 7.
Pei-Feng Liu et al., "Drug Repurposing Screening Identifies Tioconazole as an ATG4 Inhibitor that Suppresses Autophagy and Sensitizes Cancer Cells to Chemotherapy," Theranostics, Jan. 1, 2018, pp. 830-845, vol. 8, Issue 3.
Hsueh-Wei Chang et al., "Xanthium strumarium Fruit Extract Inhibits ATG4B and Diminishes the Proliferation and Metastatic Characteristics of Colorectal Cancer Cells," Toxins, Jun. 2, 2019, pp. 1-16, vol. 11(6):313.
Robin Mathew et al., "Autophagy Suppresses Tumorigenesis Through Elimination of p62," Cell, Jun. 12, 2009, pp. 1062-1075, vol. 137(6).

(Continued)

*Primary Examiner* — Ronald T Niebauer
(74) *Attorney, Agent, or Firm* — Lippes Mathias LLP

(57) ABSTRACT

The present invention relates to an isolated peptide, an anti-cancer medicinal composition including the same and a method of specifically reducing or inhibiting activities of cancer cells using the same. The isolated peptide including a TAT basic domain conjugated to a GABARAPL2 H2 domain can specifically reduce or inhibit an activity of cancer cells, thereby being applied to the anti-cancer medicinal composition and the method of specifically reducing or inhibiting activities of cancer cells using the same.

4 Claims, 12 Drawing Sheets
(2 of 12 Drawing Sheet(s) Filed in Color)
Specification includes a Sequence Listing.

(56) References Cited

OTHER PUBLICATIONS

Noboru Mizushima et al., "Methods in Mammalian Autophagy Research," Cell, Feb. 5, 2010, pp. 313-326, vol. 140(3).

Kumar Sanjiv et al., "The novel DNA alkylating agent BO-1090 suppresses the growth of human oral cavity cancer in xenografted and orthotopic mouse models," International Journal of Cancer, Apr. 15, 2011, pp. 1440-1450, vol. 130.

Chandra B Lebovitz et al., "Cross-cancer profiling of molecular alterations within the human autophagy interaction network," Autophagy, Jul. 24, 2015, pp. 1668-1687, vol. 11, Issue 9.

Mafalda Rizzuti et al., "Therapeutic applications of the cell-penetrating HIV-1 Tat peptide," Drug Discovery Today, Jan. 2015, pp. 76-85, vol. 20, No. 1.

Hongping Jin et al., "Tat-Based Therapies as an Adjuvant for an HIV-1 Functinal Cure," Viruses, Apr. 8, 2020, pp. 1-18, vol. 12(4):415.

Chih-Wen Shu et al., "High-Throughput Fluorescence Assay for Small-Molecule Inhibitors of Autophagins/ Atg4," Journal of Biomolecular Screening, Jan. 18, 2011, pp. 174-182, vol. 16(2).

Eric Hervouet et al., "The autophagy GABARAPL1 gene is epigenetically regulated in breast cancer models," BMC Cancer, Oct. 17, 2015, pp. 1-13, vol. 15:729.

Wesch et al. ('Atg8-family proteins—structural features and molecular interactions in autophagy and beyond' Cells v9 2020 pp. 1-25) (Year: 2020).

* cited by examiner

FIG. 1

ISOLATED PEPTIDE, ANTI-CANCER MEDICINAL COMPOSITION INCLUDING THE SAME AND METHOD OF SPECIFICALLY REDUCING OR INHIBITING ACTIVITIES OF CANCER CELLS USING THE SAME

CROSS-REFERENCE TO RELATED APPLICATION

This application is a divisional of U.S. patent application Ser. No. 17/096,463, filed Nov. 12, 2020. The entirety of each of these applications is hereby incorporated by reference, including the sequence listings.

BACKGROUND

A sequence listing is being submitted herein as an ASCII text file named "SP-5261-1-US_SEQ_LIST.txt", created on Jun. 2, 2022, with a file size of 8,690 bytes.

Field of Invention

The present invention relates to an anti-cancer peptide and an application thereof. More specifically, the present invention relates to an isolated peptide, an anti-cancer medicinal composition including the same and a method of specifically reducing or inhibiting activities of cancer cells using the same.

Description of Related Art

Autophagy is an evolutionarily conserved process that delivers damaged proteins and organelles from autophagosome to lysosome during times of nutrient deprivation in the cells. This evolutionarily conserved process plays an important role in many diseases, particularly in cancer development. At least thirty-eight ATG genes are primarily involved in the progression of autophagy from phagophore initiation to autophagosome formation in mammalian cells. Among them, ATG4 is the essential cysteine protease required for the activation of MAP1LC3 precursor (proMAP1LC3) and the delipidation of MAP1LC3-II from autophagosomes for its recycling to facilitate autophagy. There are 4 independent genes encoding ATG4 (4A/autophagin-2, 4B/autophagin-1, 4C/autophagin-3, and 4D/autophagin-4) in the human genome. ATG4B shows the most active and broadest proteolysis activity on human ATG8 orthologs, including MAP1LC3A, MAP1 LC3B, MAP1LC3C, GBR, GBRL1, and GBRL2.

Regarding the role of ATG4 in cancer cells, ATG4B expression in significantly elevated in tumor tissues in patients with colorectal cancer, oral cancer and CD34+ chronic myeloid lymphoma (CML). ATG4B overexpression is associated with cell necrosis induced in aggressive melanoma. Silencing ATG4B decreases tumor growth of osteosarcoma. Reconstitution of ATG4B$^{C74A}$ mutant arrest cell cycle at $G_1$ phase, indicating proteolysis of ATG4B is essential for tumor growth. Besides, ATG4A mutation is associated with cervical cancer. ATG4A is hypomethylated in ovarian tumor-initiating cells and linked to poor prognosis of ovarian cancer patients. Moreover, ATG4A expression has been found to be crucial for tumorigenic regulation of breast cancer stem cells in vivo. Ectopic expression of ATG4C facilitates ATM-mediated autophagy and cancer stemness in breast cancer cells. More interestingly, ATG4B knockout mice only show a slight defect on otoconial development of the inner ear, without growth inhibition or other clear abnormalities. These results reveal that ATG4 might be a potential drug target for cancer therapy. However, there is less studies of ATG4 as a potential drug target for cancer therapy.

Accordingly, there is an urgent need to find a resolution to better inhibition of ATG4 proteolytic activity and cancer cell suppression in cancer therapy.

SUMMARY

The invention provides an isolated peptide, which includes a HIV-1 TAT basic domain conjugated to a GABARAPL2 alpha-helix 2 (H2) domain, thereby specifically reducing or inhibiting an activity of cancer cells.

Moreover, the invention also provides an anti-cancer medicinal composition comprising an isolated peptide contained in a pharmaceutically acceptable carrier.

Furthermore, the invention also provides a method of specifically reducing or inhibiting activities of cancer cells, which includes administration of a pharmaceutically effective dose of an isolated peptide of SEQ ID NO: 10 to a subject in need thereof, and the isolated peptide has an ability of specifically reducing or inhibiting an activity of the cancer cells.

According to the aforementioned aspect, the invention provides an isolated peptide. In an embodiment, the isolated peptide can include a HIV-1 TAT basic domain conjugated to a N-terminus of a GABARAPL2 alpha-helix 2 (H2) domain. The GABARAPL2 H2 domain can be consisting of an amino acid sequence of SEQ ID NO: 1.

In the aforementioned embodiment, the HIV-1 TAT basic domain can be consisting of an amino acid sequence of SEQ ID NO:2. In some examples, the isolated peptide can optionally comprise a peptide linker interposed between the TAT basic domain and the GABARAPL2 H2 domain, and the peptide linker can include but be not limited to a glycine-rich peptide, a Gly/Ser rich peptide or a Gly/Ala rich peptide. In certain examples, the peptide linker can include a sequence selected from the group consisting of amino acid sequences of SEQ ID NOs:3 to 9. In an example, the isolated peptide can be consisting of an amino acid sequence of SEQ ID NO: 10.

According to yet another aspect, the invention provides an anti-cancer medicinal composition. In an embodiment, the anti-cancer medicinal composition can include an isolated peptide contained in a pharmaceutically acceptable excipient. In the embodiment, the isolated peptide can be an active agent, and the isolated peptide can be consisted of an amino acid sequence of SEQ ID NO: 10.

According to yet further aspect, the invention provides a method of specifically reducing or inhibiting activities of cancer cells. In an embodiment, the method can administer a pharmaceutically effective dose of an isolated peptide of SEQ ID NO: 10 to a subject in need thereof.

In the aforementioned embodiment, a type of the cancer cells can include but be not limited to colorectal cancer, glioblastoma, oral cancer, hepatocellular carcinoma, breast cancer, prostate cancer and lung cancer.

In the aforementioned embodiment, the isolated peptide can have an ability of specifically reducing or inhibiting an activity of cancer cells.

In the aforementioned embodiment, the activity of the cancer cells can include but be not limited to ATG4 proteolytic activity, cell migration, invasion and stemness.

With application to the isolated peptide, the anti-cancer medicinal composition including the same and the method of specifically reducing or inhibiting activities of cancer cells using the same, the isolated peptide including the HIV-1 TAT basic domain conjugated to GABARAPL2 H2 domain can specifically reduce or inhibit an activity of cancer cells, thereby being applied to the anti-cancer medicinal composition for specifically reducing or inhibiting activities of cancer cells using the same.

It is to be understood that both the foregoing general description and the following detailed description are by examples, and are intended to provide further explanation of the invention as claimed.

BRIEF DESCRIPTION OF THE DRAWINGS

The patent or application file contains at least one drawing executed in color. Copies of this patent or patent application publication with color drawings will be provided by Office upon request and payment of the necessary fee. The disclosure can be more fully understood by reading the following detailed description of the embodiment, with reference made to the accompanying drawings as follows.

FIG. 1 depicts a protein sequence alignment of human ATG8 orthologs, including MAP1LC3 (MLP3A, B, C as listed in SEQ ID NOs: 17, 18, 16, respectively) and GBR (GBR, GBRL1, GBRL2 as listed in SEQ ID NOs: 14, 15, 13, respectively) subfamilies according to several embodiments of the present invention. H1 (as listed in SEQ ID NO: 11), H2 (as listed in SEQ ID NO: 1) and H3 (as listed in SEQ ID NO: 12) are α-helical regions in protein structure.

FIGS. 2A and 2B illustrate three α-helical peptides (H1, H2 and H3) derived from GBRL2, which were 2-fold serial titrated and mixed with recombinant ATG4A (5 nM) (FIG. 2A) or recombinant ATG4B (0.1 nM) (FIG. 2B) in the presence of 100 nM reporter GBRL2-PLA2, a general substrate for ATG4 members, to evaluate the inhibitory effect of peptides on ATG4A and ATG4B. The $IC_{50}$ of peptides on ATG4B and ATG4A was analyzed by Prism 5.0. FIG. 2C illustrates the inhibitory activity of EDTA on proteolysis of ATG4 as a positive control in the upper panel. In the lower panel of FIG. 2C, the H2 peptide was further counter assayed with 0.5 nM caspase-3 and 100 μM DEVD-AFC to validate its specificity.

FIG. 3A depicts H2 peptides derived from different ATG4 substrates, including MAP1LC3B, MAP1LC3C and GBR, GBRL2 were mixed with chimeric GBRL2 containing N-terminal C-myc tag and C-terminal S-tag. The S-tag GBRL2 in the upper panel and ratios of non-cleaved/cleaved Myc-tag GBRL2 in the lower panel are used to evaluate the inhibitory effects of the H2 peptides. FIG. 3B depicts human glioblastoma H4 cells and colorectal cancer HCT116 cells both treated with 10 μM GBRL2 H2 peptide alone (orange) or TAT peptide alone (red) or GBRL2 H2 peptide conjugated with TAT peptide (green) for 6 hours and analyzed with flow cytometer. FIG. 3C depicts the HCT116 cells expressing ATG4 cleavable luciferase treated with GBRL2 H2 peptide for 6 hours. The luciferase activity is measured to determine the inhibitory effects on cellular ATG4 proteolysis.

FIG. 5A depicts the invasion of HCT116 cells examined with Matrigel-coated Transwell filters in the presence or absence of peptides, and the cell invasion results are quantified with ImageJ software. FIG. 5B depicts the quantified results for invasion expressed as the mean±SEM. *$p<0.05$; **$p<0.01$.

FIG. 6A depicts images of HCT116 cells seeded on NanoCulture plates for 3 days to grow sphere that are treated with GBRL2 or TAT-GBRL2 peptides for 3 or 7 days using TAT peptide as a control. FIG. 6B depicts sphere viability measured by a 3D CellTiter Glo assay and expressed as a percentage compared with cells exposed to the same concentration of TAT peptide. FIG. 6C depicts images of the tumorspheres treated with the peptides (20 μM) as above for 7 days and the live (green) or dead (red) sphere proportion determined using LIVE/DEAD Cell Viability Assays. FIG. 6D depicts the proportion of live and dead tumorsphere quantified from three independent experiments. FIG. 6E depicts HCT116 cells stably expressing firefly luciferase xenografted into nude mice for a week until tumor formation. The mice are intratumorally (IT, n=5) or intraperitoneally (IP, n=5) administrated with the peptides for 7 or 14 days. The tumor viability in mice is monitored with administration of D-luciferin (150 mg/kg) using a non-invasive imaging system. FIG. 6F depicts the quantitative result for tumor viability in xenograft mice. *$p<0.05$; $p<0.01$; *$p<0.001$.

DETAILED DESCRIPTION

Figure 2A:
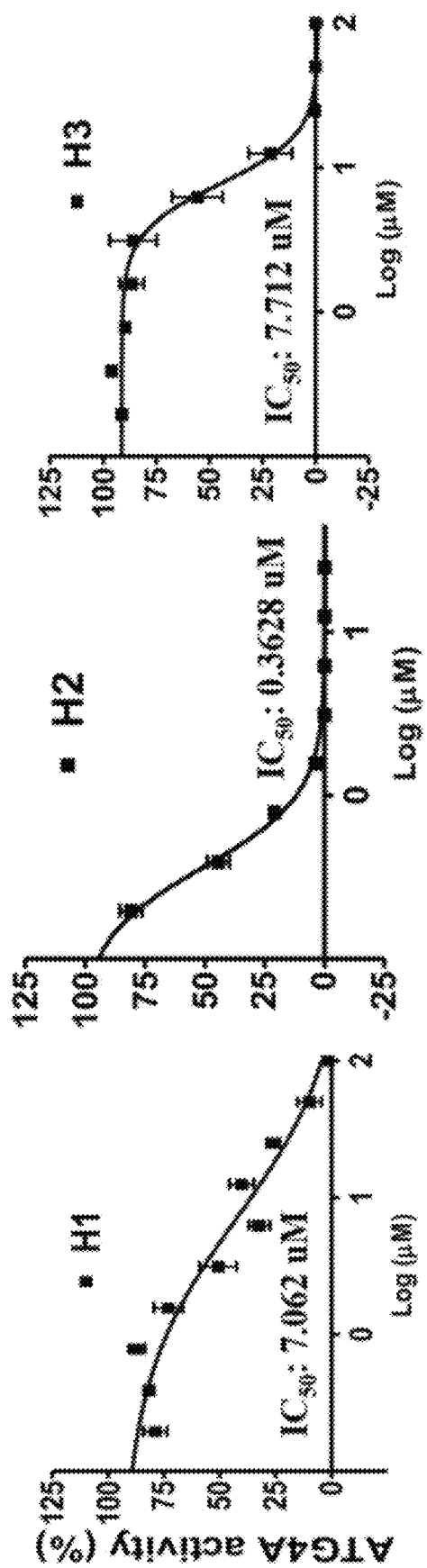
FIGS. 2A to 2C illustrate the inhibitory effects of GBRL2-derived peptides on ATG4 proteolytic activity according to several embodiments of the present invention.

Reference will now be made in detail to the present embodiments of the invention, examples of which are illustrated in the accompanying drawings. Wherever possible, the same reference numbers are used in the drawings and the description to refer to the same or like parts. Various terms used throughout this specification shall have the definitions set out herein.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids. The amino acids may be L- or D-amino acids. An amino acid may be replaced by a synthetic amino acid which is altered so as to increase the half-life of the peptide or to increase the potency of the peptide, or to increase the bioavailability of the peptide.

The term "peptide" as used herein, refers to a molecule of two or more amino acid chemically linked together. A peptide may refer to a polypeptide, protein or peptidomimetic. The peptides of the invention may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. The term "peptide" is also inclusive of modifications including, but not limited to, glycosylation, lipid attachment, sulfation, gamma-carboxylation of glutamic acid residues, hydroxylation and ADP-ribosylation. In some embodiments, the peptide is of any length or size. Use herein of the terms "peptide", "peptides", or "peptidomimetic" should be taken to include reference to "derivatives" of such compounds, unless the context requires otherwise, and to include "prodrugs". The term "peptidomimetic" as used herein refers to a small protein-like chain designed to mimic a peptide. A peptidomimetic typically arises from modification of an existing peptide in order to alter the molecule's properties.

The term "isolated peptide" as used herein, refers to a peptide that is substantially pure and is free of other substances with which it is ordinarily found in nature or in vivo systems to an extent practical and appropriate for its intended use. For example, the compositions are sufficiently pure and are sufficiently free from other biological constituents of host cells so as to be useful in, for example, producing pharmaceutical preparations or sequencing.

In some embodiment, the isolated peptide of the present invention includes a HIV-1 TAT basic domain conjugated to a GABARAPL2 alpha-helix 2 (H2) domain, optionally a peptide linker interposed therebetween.

In these embodiments, the GABARAPL2 H2 domain can be consisted of an amino acid sequence of SEQ ID NO: 1, which corresponds to the 57th to the 67th amino acid residues of the GABARAPL2.

The HIV-1 TAT basic domain is consisted of an amino acid sequence of SEQ ID NO: 2, which corresponds to the 47th to 57th amino acid residues (or called as protein transduction domain, PTD) of the HIV-1 TAT protein.

In certain embodiments, the isolated peptide can optionally comprise a peptide linker interposed between the TAT basic domain and the GABARAPL2 H2 domain. In these embodiments, the peptide linker can include but be not limited to a glycine-rich peptide, a Gly/Ser rich peptide or a Gly/Ala rich peptide, without inducing conformational changes of the TAT basic domain and the GABARAPL2 H2 domain. In certain examples, the peptide linker can include but be not limited to a sequence selected from the group consisting of amino acid sequences of SEQ ID NOs:3 to 9. In some examples, the isolated peptide can be consisting of an amino acid sequence of SEQ ID NO: 10, or called as TAT-GBRL2 peptide.

In some embodiments, an anti-cancer medicinal composition can be provided. In these embodiments, the anti-cancer medicinal composition can include the aforementioned isolated peptide contained in a pharmaceutically acceptable excipient. In these embodiments, the isolated peptide can be an active agent, and the isolated peptide can be consisted of an amino acid sequence of SEQ ID NO: 10.

The term "subject" or "patient" or "individual", as used herein, refers to a eukaryote. A biological sample is typically obtained from a eukaryotic organism including, but not limited to, mammals. Mammalian subjects include, but are not limited to, primates such as a human; non-human primates including chimpanzees and the like; livestock, including but not limited to, cows sheep, pigs, and the like; companion animals, including but not limited to, dogs, cats, horses, rabbits, rodents including mice and rats, and the like.

The term "active agent" as used herein, refers to the isolated peptide, ingredient, component or constituent of the compositions of the present invention responsible for the intended therapeutic effect, such as anti-cancer regimens contributed by the decrease or inhibition of an activity or function of the cancer cells specifically. In some embodiments, the isolated peptide can have an ability of specifically reducing or inhibiting an activity or function of cancer cells, thereby being as an ATG4 inhibitor, a tumor repressor or an anticancer agent.

The term "cancer" as used herein is defined as proliferation of cells whose unique trait—loss of normal controls— results in unregulated growth, lack of differentiation, local tissue invasion, and metastasis. Examples include but are not limited to, colorectal cancer, glioblastoma, oral cancer, hepatocellular carcinoma, breast cancer, prostate cancer and lung cancer.

The term "anti-cancer effect" as used herein, refers to the isolated peptide or a composition including the same that specifically (or selectively) reduces, inhibits or represses the activity or function of cancer cells, for example, inhibits their ATG4 proteolytic activity, cell migration, invasion, stemness, and/or causes their destruction in vitro or in vivo, without affecting the normal cells. In one embodiment, the isolated peptide or the medicinal composition including the same can be administered before, during or after administration of conventional anti-cancer drugs.

In some embodiments, a method of specifically reducing or inhibiting activities of cancer cells using the aforementioned isolated peptide and/or the anti-cancer medicinal composition is provided. In these embodiments, the method can administer a pharmaceutically effective dose of an isolated peptide of SEQ ID NO: 10 to a subject in need thereof.

The term "administer", "administering" or "to administer" as used herein, refers to the giving or supplying of the isolated peptide or the medicinal composition, including in vivo administration, as well as administration directly to tissue ex vivo. Generally, compositions may be administered systemically either orally, buccally, parenterally, topically, by inhalation or insufflation (i.e., through the mouth or the nose) or rectally in dosage unit formulations containing conventional nontoxic pharmaceutically acceptable excipient, carriers, adjuvants and vehicles as desired, or may be locally administered by means such as, but not limited to, injection, implantation, grafting, topical application or parenterally.

The term "reduce (inhibit or repress)", "reducing (inhibiting or repressing)", "reduced (inhibited or repressed)" or "to reduce (to inhibit or to repress)" as used herein, refers to a diminishing, a decrease in, an attenuation or abatement of the degree, intensity, extent, size, amount, density or number.

The term "pharmaceutically effective dose" or "dosage" as used herein, generally refers to the amount of the isolated peptide applied to the target cells or the subject for a period of time in order to provide one or more clinically measurable endpoints, such as reducing or inhibiting an activity or function of the cancer cells of the subject. There is no specific limitation to a dosage of the isolated peptide in the anti-cancer medicinal composition; however, in some examples, the isolated peptide can be administered in 1-20 µM in vitro or 5-50 mg/kg body weight in vivo. Besides, there is no specific limitation to the period depending on the target cells or the subject.

Thereinafter, it will be understood that particular configurations, aspects, examples, clauses and embodiments described hereinafter are shown by way of illustration and not as limitations of the invention. The principal features of this invention can be employed in various embodiments without departing from the scope of the invention. Thus, one skilled in the art can easily ascertain the essential characteristics of the present invention and, without departing from the spirit and scope thereof, can make various changes and modifications of the invention to adapt it to various usages and conditions.

Example 1

1.1 Peptide Synthesis

Peptides were synthesized by Lifetein (CA, USA) and purified to >95% by HPLC (confirmed by mass spectrometry). The inhibitory peptide sequence derived helical regions from H1 (LEHRCVESAKIRAK, SEQ ID NO:11), H2 (VAQFMWIIRKR, SEQ ID NO:1) and H3 (MGQLYEKE, SEQ ID NO:12) for GBRL2. The H2 peptide was conjugated with the Tat penetration domain (YGRKKRRQRRR, SEQ ID NO:2) at the N terminus and a GGS linker to increase flexibility. All the peptides were modified with N-terminal acetylation and C-terminal amidation to increase stability. The synthesized peptides were dissolved in DMSO and stored at −20° C. until use.

1.2 ATG4 Activity Measured Using GATE16-PLA$_2$ Substrate

The reporter assay was modified from a previous report. Briefly, recombinant ATG4A or ATG4B was mixed with 100 nM GBRL2-PLA$_2$ fusion protein in 20 µL PLA$_2$ reaction buffer containing 20 mM Tris-HCl, pH 8.0, 2 mM CaCl$_2$) and 1 mM DTT, and 20 µM 2-(6-(7-nitrobenz-2-oxa-1,3-diazol-4-yl)amino)hexanoyl-1-hexadecanoyl-sn-glycero-3-phosphocholine (NBD-C$_6$-HPC) (Invitrogen, N-3786). Fluorescence intensity was measured within 30-60 minutes using Fluoroskan Ascent FL Reader (Thermo Fisher Scientific) at room temperature with excitation and emission wavelength of 485 nm and 530 nm, respectively. The IC$_{50}$ of peptides on GBRL2-PLA$_2$ was determined using nonlinear regression fitting of a series of progress curves.

1.3 Cell Culture for Regular Maintenance

Cancer cell lines were purchased from American Type Culture Collection and these cells were grown in DMEM/F12 (Invitrogen-Gibco, Carlsbad, USA), with 10% heat-inactivated fetal bovine serum (Biological Industries, Kibbutz Beit-Haemek, Israel), 100 U/mL penicillin (Invitrogen-Gibco, Carlsbad, USA), and 100 µg/mL streptomycin (Invitrogen-Gibco, Carlsbad, USA), at 37° C. in a humidified 5% CO$_2$ atmosphere. Cells were grown in Corning tissue culture-treated plastic (Corning, Inc., Corning, USA).

1.4 Cell Transfection and Stable Selection

For transient knockdown, cells were transfected with RNAiMAX (Life technologies) in the presence of 5 nM pooled scramble siRNA or siRNA against ATG4B (ambion). To generate stable silenced cell line, HEK293FT cells were transfected with Lentivrial vector containing luciferase expression gene with Lipofectamine 2000 (Life technologies) for 2 days to collect supernatant containing virus particles. The supernatant was filtered and infected to cancer cells and further selected with 1-3 µg/mL puromycin. The medium containing puromycin was renewed every 2-3 days for at least 2 weeks and the stable luciferase expressing cells were selected.

1.5 MAP1LC3-Luc Cleavable Assay to Monitor ATG4s Activity in HEK293T Cells

The plasmid MAP1LC3 wt-Luc or MAP1LC3 G120A-Luc (as a normalization control) was transfected into HEK293T (2000 cells/40 µL) seeded in 384-well white plates for overnight. The cells were treated with ATG4 inhibitors for 8 hours or 16 hours, followed by adding 200 µM D-luciferin (Promega) into each well to monitor the luciferase activity to reflect ATG4 activity in cells. Since protein level significantly decreased after knockdown of ATG4B for 48 hours, luminescent signal (RLU) was monitored between 48 hours and 72 hours for use as a positive control. Net RLU of silencing ATG4B was used as a threshold to evaluate effect of inhibitors on ATG4 activity in cells.

1.6 Spheroid Cell Culture and Live/Dead Assay

The trypsinized cells were resuspended in PBS containing 2% FBS for cell counting. The cells (4000 cells/well) then were seeded into a 24-well plate (1.9 cm$^2$, SCIVAX Corporation, Kanagawa, Japan) with tumorsphere culture medium [advanced DMEM-F12 (Gibco), 2 mmol/L of L-glutamine, 100 Unit/mL of penicillin and streptomycin, N2 supplement (Gibco), 20 ng/mL of epidermal growth factor (R&D) and 10 ng/mL of fibroblast growth factor-basic (R&D)] and grown 7 days to form spheroid cells. The sphere viability can be measured by CellTiter Glo 3D (Promega). Alternatively, the live and dead spheroid cells were stained every other day with Calcein AM (1 µM) and Ethidium homodimer-1 (EthD-1, 2 µM) (LIVE/DEAD® Viability/Cytotoxicity Kit, ThermoFisher Scientific) for 30 minutes. The live (green) and dead spheroid cells were imaged via fluorescence microscopy and quantitated using a Fluoroskan Ascent FL reader (Thermo Fisher Scientific) with excitation at 485 nm and emissions at 530 nm and 645 nm for calcein AM and EthD-1, respectively.

1.7 Xenograft Mouse Model

Age-matched female nude mice (6-8 weeks old) were used in assays for tumor growth and metastasis in a xenograft model. All experiments were performed as approved by Institutional Animal Care and Use Committee. HCT116 cancer cells (2×10$^6$ cells in 0.05 mL of PBS) expressing luciferase was mixed with matrigel (PBS:Matrigel=1:1) and injected into mice (n=5/group) subcutaneously. The mice were injected with PBS or peptides intratumorally (5 mg/kg) or intraperitoneally (50 mg/kg) every other day. The tumors were intraperitoneally administrated with D-luciferin (150 mg/kg) and then monitored by using a non-invasive imaging system (Xenogen IVIS-200 system) once a week. The data was reported as luminescent intensity from a defined region for primary tumors compared to control mice.

1.8 Statistics

All data was presented as mean±SEM from samples or experiments of at least 3 replicates unless stated otherwise. Results from student t-tests with p<0.05 were considered significant. *p<0.05; **p<0.01.

Example 2: Evaluation of Anti-Cancer Effects of TAT-GBRL2 Peptide on Cancers

Results

Figure 1:
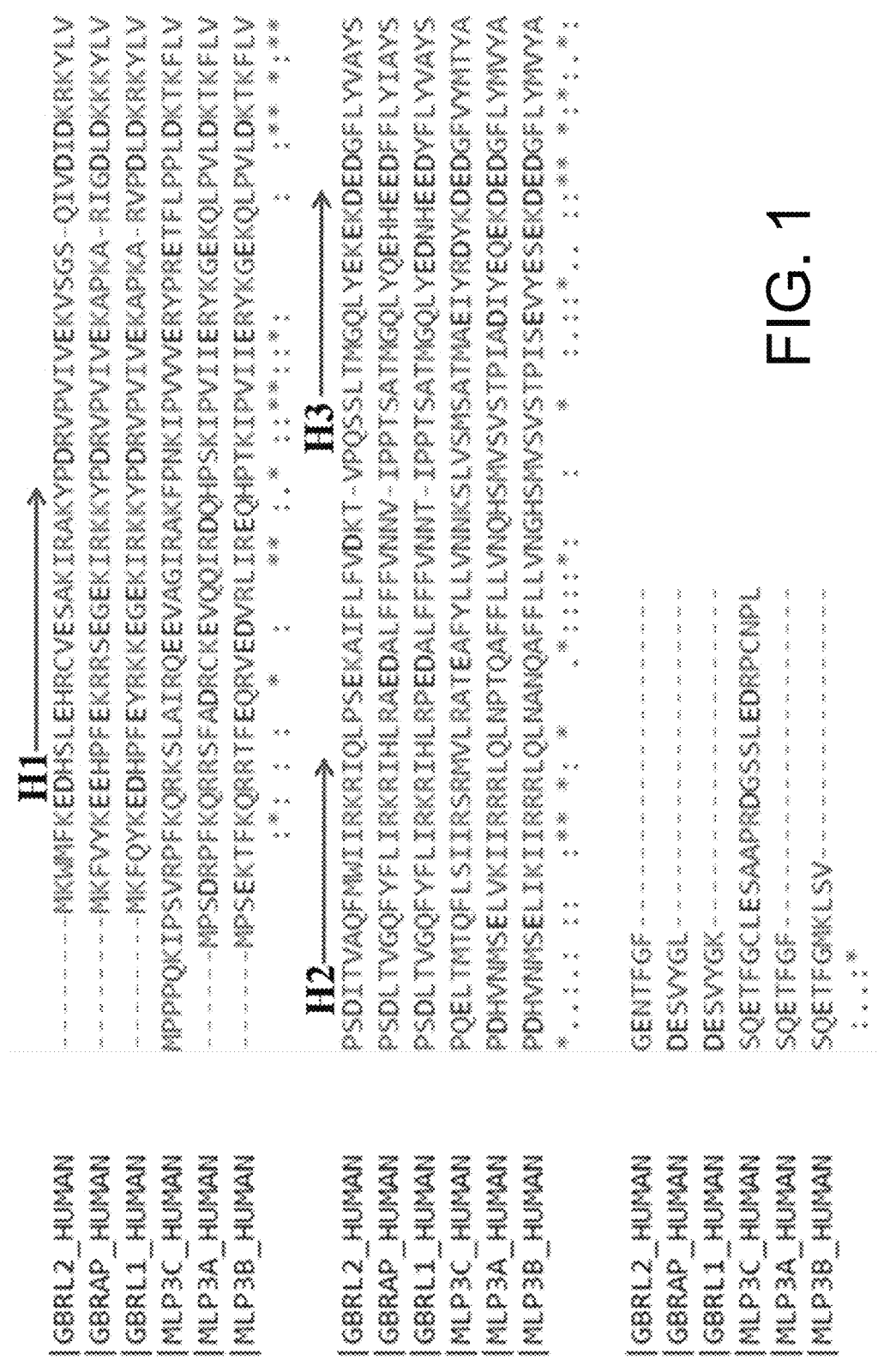
Figure 2B:
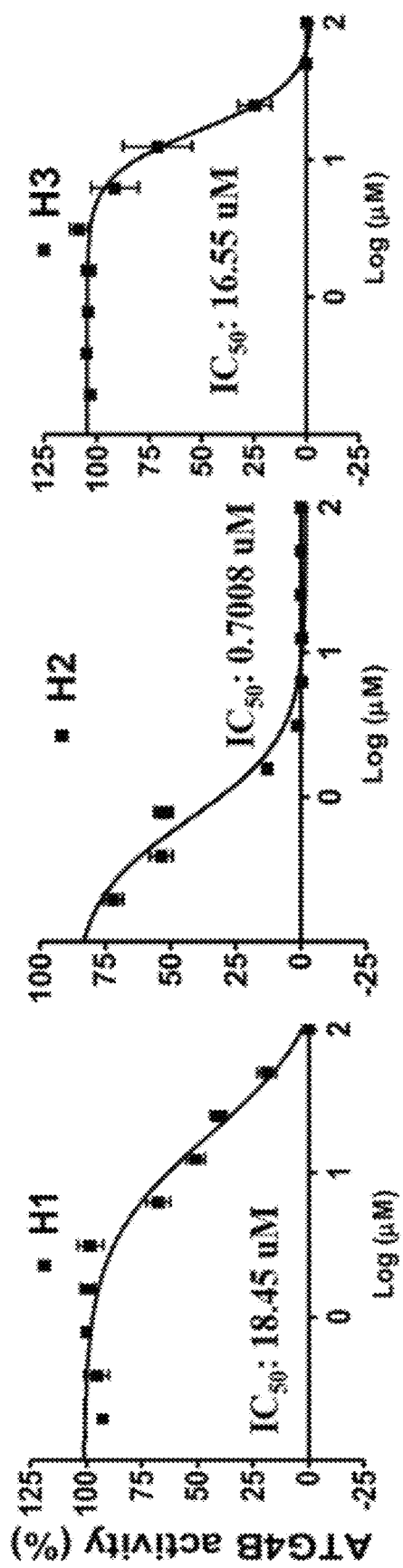
Figure 2C:
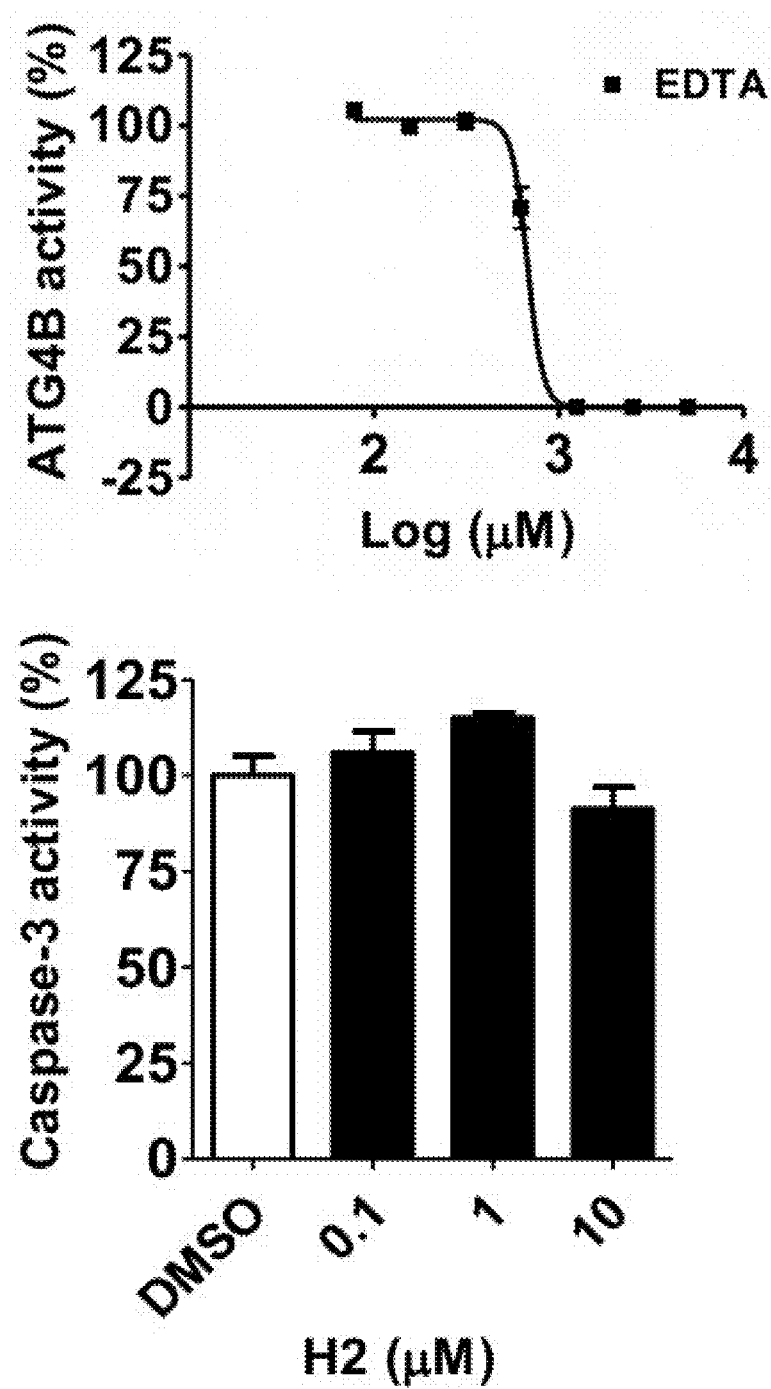

ATG4 was highly associated with tumorigenesis and poor prognosis in various cancers. Silencing ATG4B also diminished cancer cell proliferation, migration and invasion. α-helix was important for protein-protein interaction. FIG. 1 depicted a protein sequence alignment of human ATG8 orthologs, including MAP1LC3 (MLP3A, B, C, as listed in SEQ ID NOs: 17, 18, 16, respectively) and GBR (GBR, GBRL1, GBRL2, as listed in SEQ ID NOs: 14, 15, 13, respectively) subfamilies according to several embodiments of the present invention. The structure of ATG4 substrate GBRL2 was analyzed and found there are three α-helical regions in the GBRL2 protein structure (FIG. 1). Sequence alignment for six ATG4 substrates indicated that the α-helical sequences (H1, H2 and H3, as listed in SEQ ID NOs:11, 1 and 12, respectively) were almost identical in two groups (GBR/GBRL1 and MAP1LC3A/MAP1LC3B)(FIG. 1), which were closer in family tree according to protein sequence phytogram (data not shown). There were some differences in peptide sequence among the other ATG4 substrates (FIG. 1). GBRL2 was the common substrate for ATG4A and ATG4B. Thus, to examine the effects of α-helical peptides derived from GBRL2 on ATG4 proteolytic activity, three peptides with ATG4 reporter GBRL2-PLA$_2$ assay were initially tested as previous described. All the α-helical peptides (H1, H2 and H3) showed inhibitory effects on ATG4A and ATG4B proteolytic activity using EDTA as a positive control, while the H2 peptide displayed the lowest IC50 in the reporter assay (FIGS. 2A to 2B). Moreover, the H2 peptide had no effects on activity of caspase-3, another group of cysteine protease (FIG. 2C), suggesting H2 helical peptide might be able to selectively interfere the ATG4 activity.

Figure 3A:
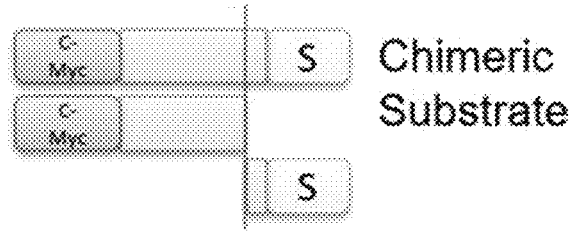
FIGS. 3A to 3C illustrate the effects of peptides on cellular ATG4 proteolysis and autophagic flux according to several embodiments of the present invention.
Figure 3A:
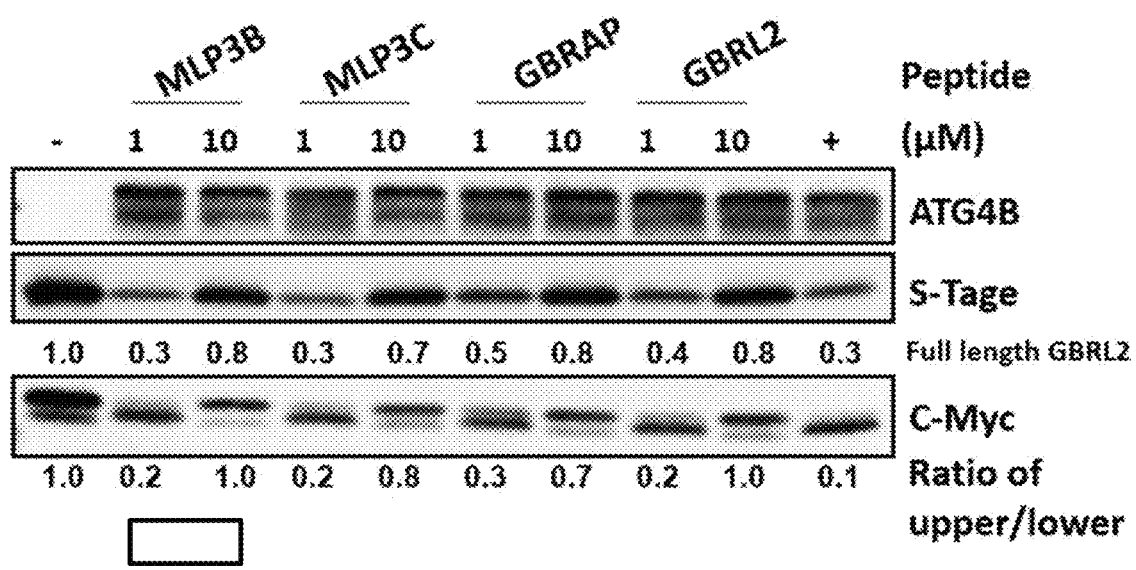

Further, H2 helical peptides from different ATG4 substrates were tested for ATG4B activity with GABARAL2 chimeric substrates, which contained N-terminal C-myc tag and C-terminal S-tag (FIG. 3A). Compared to the controls, the remaining S-tag and the ratio of full length C-myc tagged GBRL2/cleaved C-myc tagged GBRL2 levels were quantified to determine the inhibitory effects of peptides on ATG4B proteolytic activity toward GBRL2. The H2 peptides from MAP1LC3B, MAP1LC3C, GBR and GBRL2 inhibited ATG4B cleavage activity in dose dependent manner, while H2 peptides derived from MAP1LC3B and GBRL2 had the strongest inhibition on ATG4B (FIG. 3A). Thus, GBRL2-derived H2 peptides (GBRL2) were chosen for the following experiments.

Figure 3B:
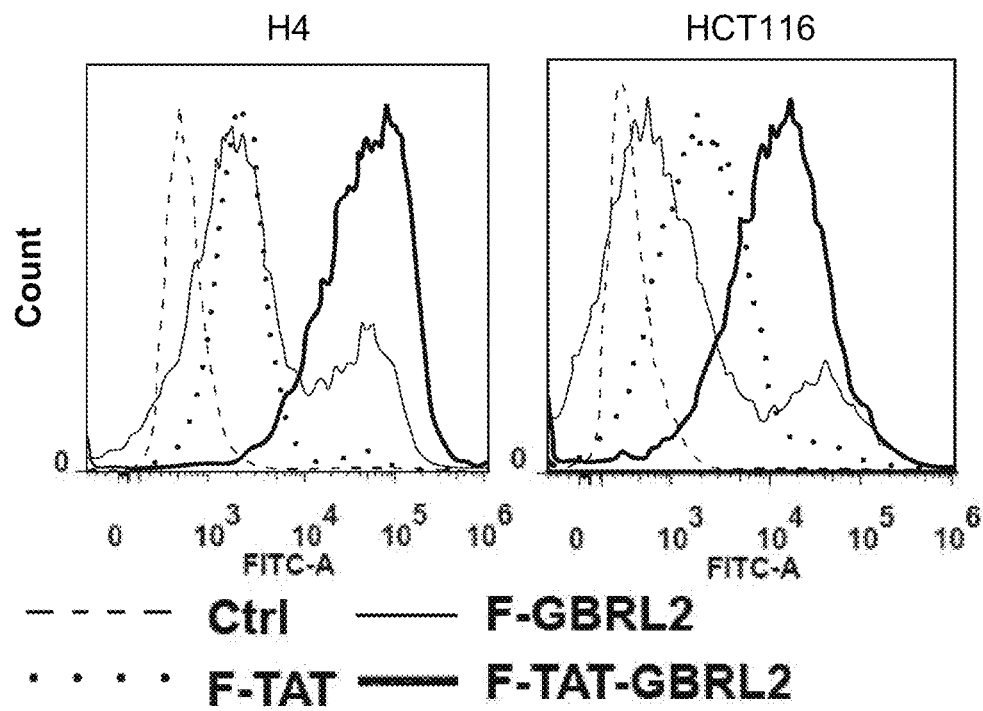
Figure 3C:
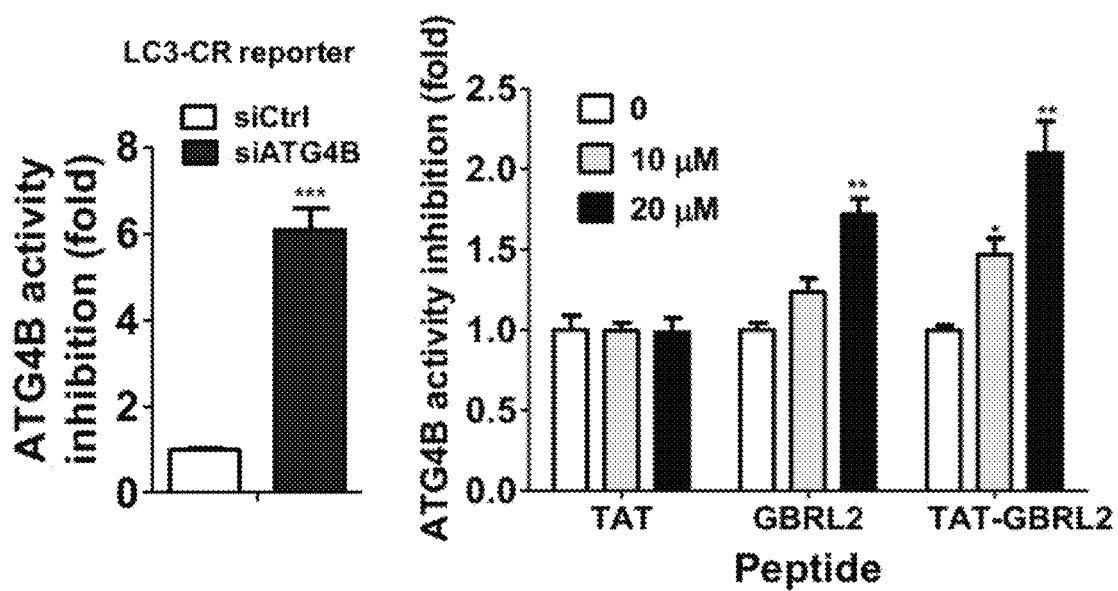

To further inspect the effects of GBRL2 peptides in cells, the peptide was labeled with FITC and fused with or without cell penetration peptide TAT1. The human glioblastoma H4 cells and colorectal cancer HCT116 cells were treated with the FITC labeled peptide to analyze the proportion of FITC positive cells with flow cytometry (FIG. 3B). The TAT-GBRL2 peptide was easier to penetrate cell membrane in both H4 and HCT116 cells compared to TAT or GBRL2 peptide. The cells expressing ATG4 cleavable luciferase was used to examine the effects of peptides on cellular ATG4 activity using ATG4B silencer as positive control (FIG. 3C). The GBRL2 and TAT-GBRL2 peptides elevated cellular luciferase activity, indicating that these peptides may inhibit cellular ATG4. In addition, cancer cells were treated with the peptides in the presence or absence of autophagy inhibitor BafA1 to determine their effects on MAP1LC3 flux (data not shown). The TAT-GBRL2 peptide significantly reduced MAP1LC3 flux in cancer cells compared to TAT peptide.

Figure 4A:
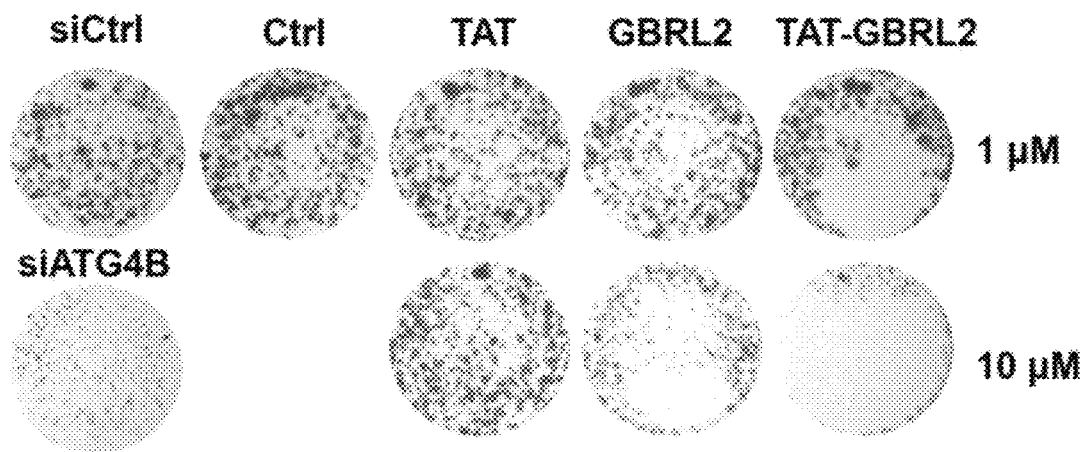
FIGS. 4A and 4B depict the cytotoxic effects of peptide (5 μM) in H4 cells (FIG. 4A) and HCT116 cells (FIG. 4B) further confirmed by clonogenic assay according to several embodiments of the present invention.
Figure 4A:
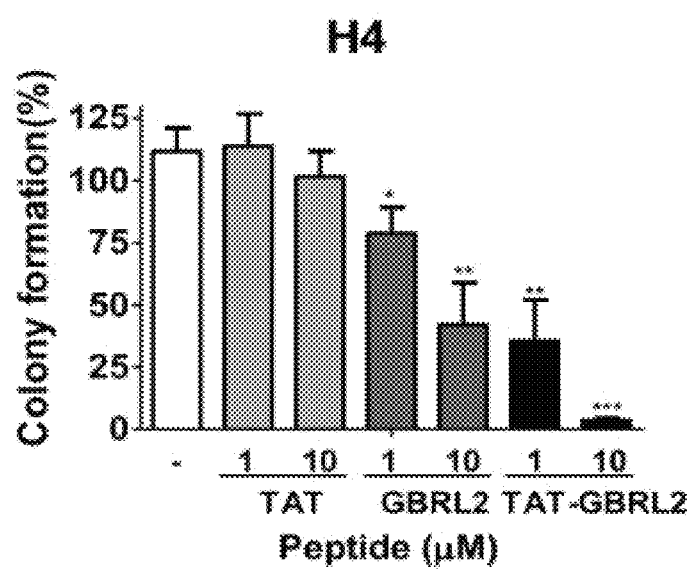
Figure 4B:
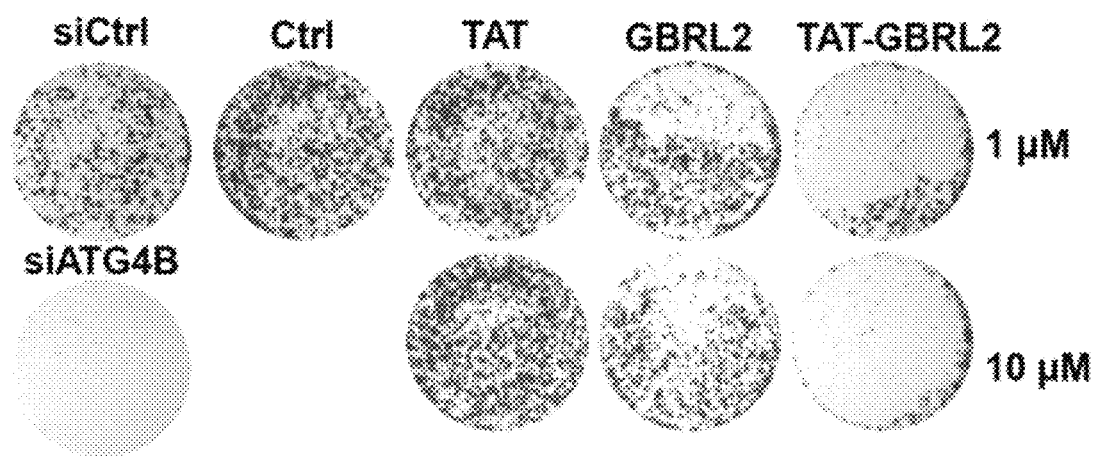
Figure 4B:
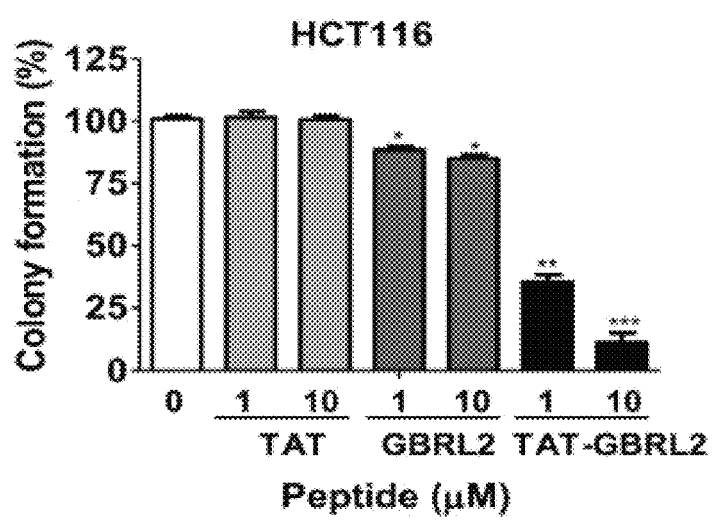

Since ATG4 might be required for cancer cell viability and metastatic characteristics, such as migration and invasion, the H4 cells and HCT116 cells were treated with peptides to determine the short- and long-term effects of peptide on cancer cells (FIGS. 4A to 4B). The TAT-GBRL2 peptide significantly decreased the cell viability of both HCT116 and H4 cells in a dose-dependent manner, whereas TAT and GBRL2 peptides had no or little effects on cell viability of cancer cells (data not shown). Likewise, results of propidium iodide (PI) uptake showed that TAT-GBRL2 peptide obviously elevated PI positive proportion of H4 and HCT116 cells (data not shown). The GBRL2 peptide slightly increased PI positive cells, but TAT peptide had no effects on PI uptake of cancer cells, suggesting GBRL2 and TAT-GBRL2 peptides induced cancer cell death. Consistently, clonogenic assay indicated that long-term treatment of GBRL2 and TAT-GBRL2 peptides reduced colony formation (FIGS. 4A and 4B).

Figure 5A:
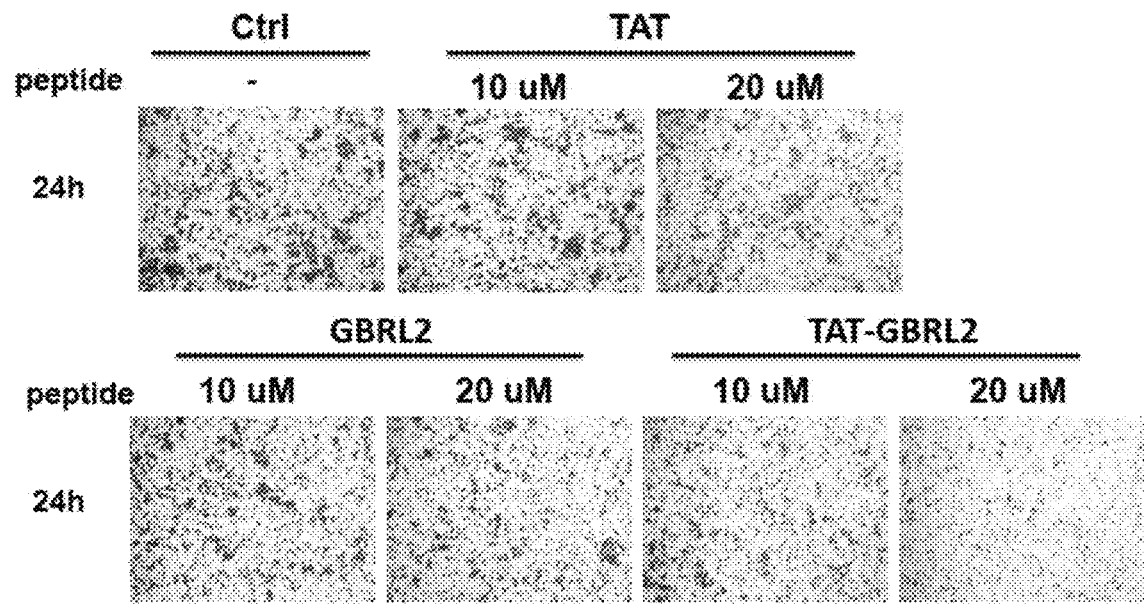
FIGS. 5A to 5B illustrate the effects of GBRL2 peptides on cancer cell migration and invasion according to several embodiments of the present invention.
Figure 5B:
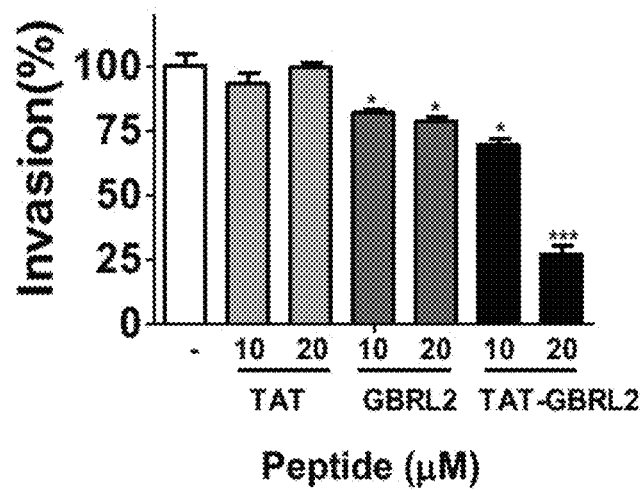

Besides the role of ATG4 in cancer cell survival, ATG4 plays a crucial role in cancer metastasis. Human glioblastoma H4 cells and colorectal cancer HCT116 cells were treated with the peptides for the cell migration assay. Higher dose (20 μM) of TAT-GBRL2 peptide inhibited cancer cell migration, the cell migration treated with the TAT or GBRL2 peptide was not altered (data not shown). Moreover, both GBRL2 and TAT-GBRL2 peptides significantly decreased the invaded HCT116 cells (FIGS. 5A and 5B).

Figure 6A:
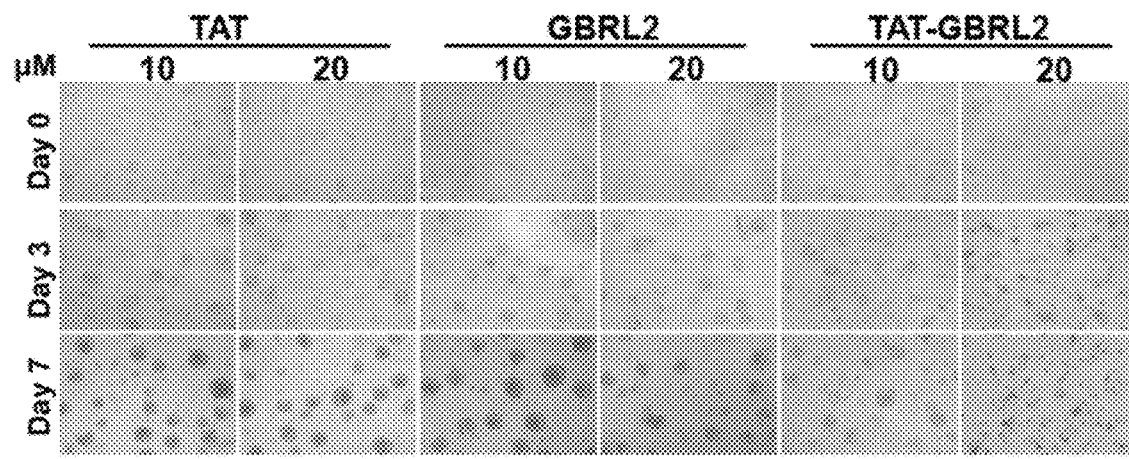
FIGS. 6A to 6F illustrate the effects of peptides on tumorsphere culture and xenograft mouse models according to several embodiments of the present invention.
Figure 6B:
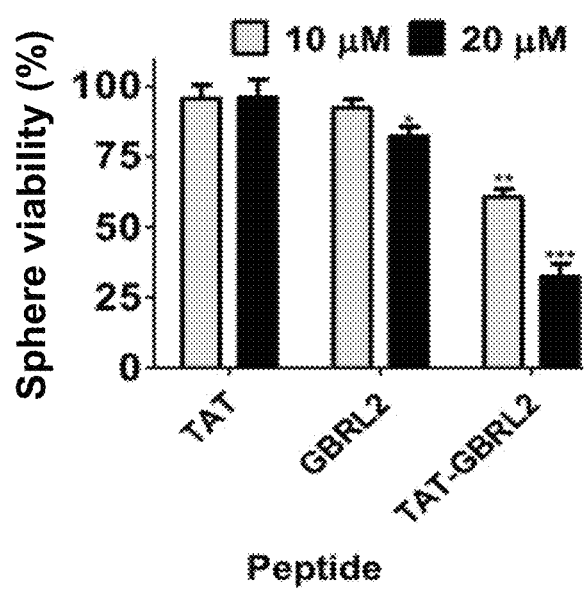
Figure 6C:
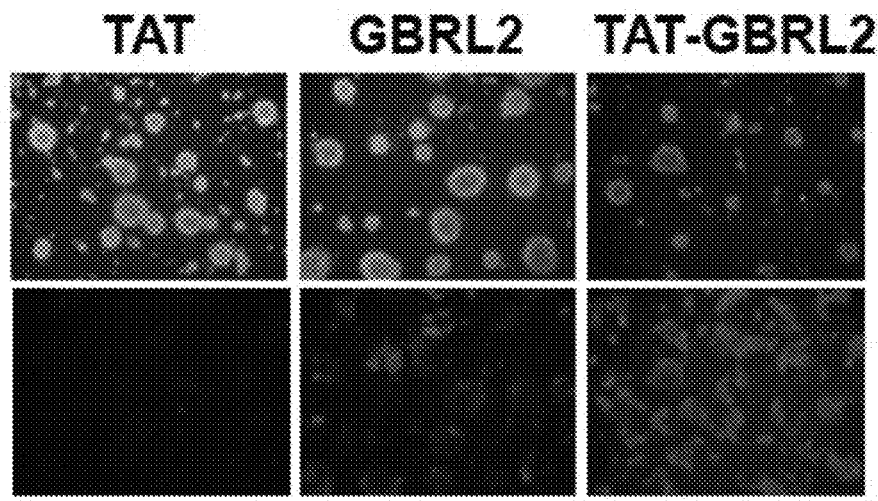
Figure 6D:
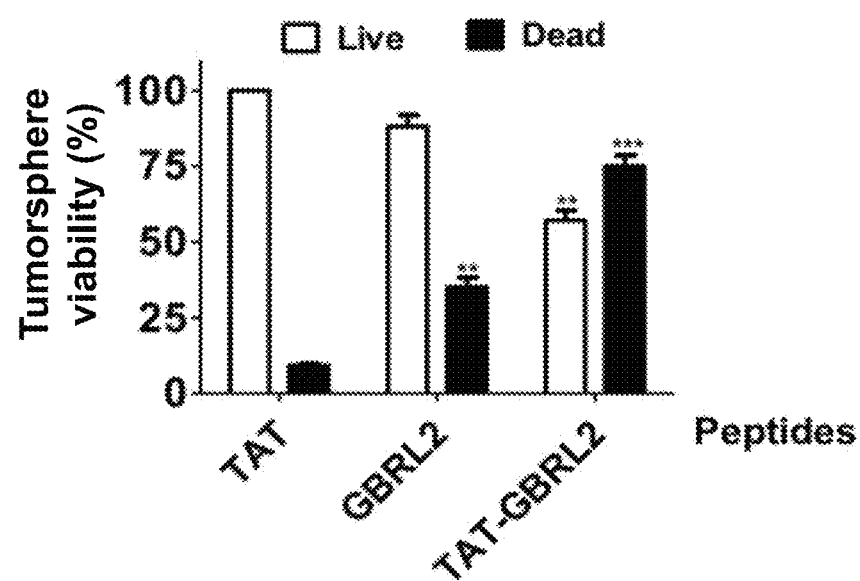
Figure 6E:
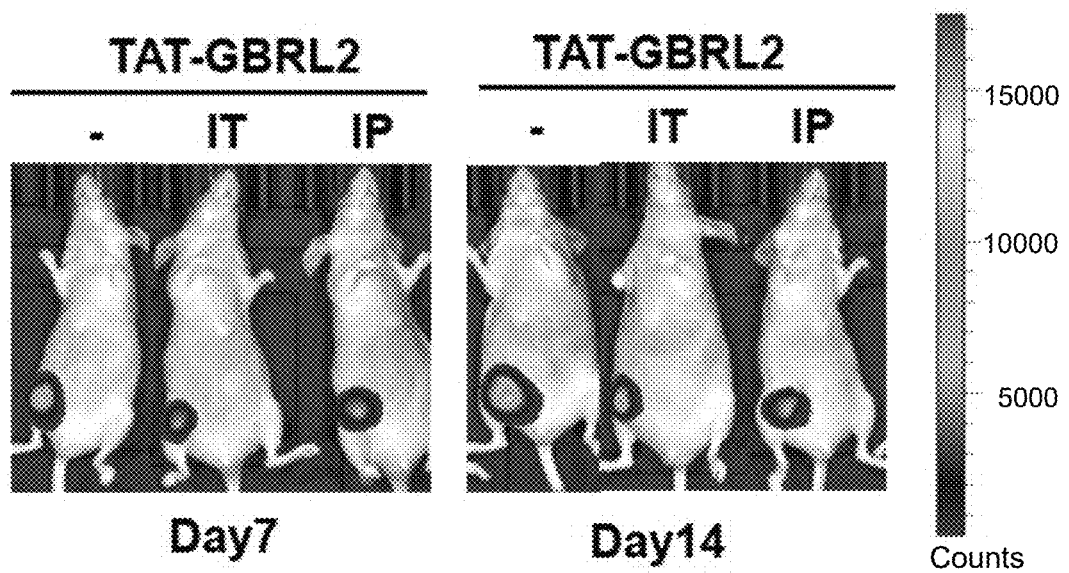
Figure 6F:
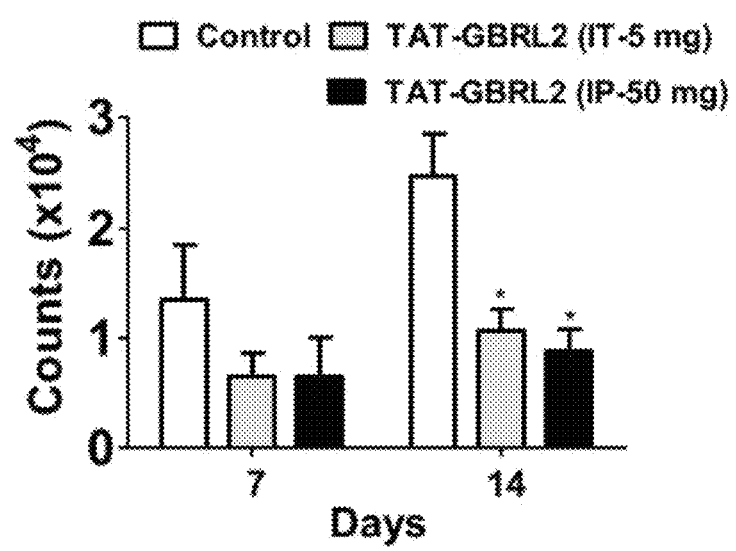

In addition, to mimic the complicated nature of cancer cells in vivo, tumor spheroid culture was used to initially examine the inhibitory effects of peptides on tumor. HCT116 cells were cultured to form tumorsphere and treated with TAT, GBRL2, and TAT-GBRL2 peptides (FIGS. 6A to 6D). It found that TAT-GBRL2 peptide significantly decreased tumorsphere viability and increased dead cells. Additionally, HCT116 cells expressing luciferase were xenografted into mice to evaluate the effects of TAT-GBRL2 peptide on tumor growth in vivo using bioluminescent imaging IVIS system (FIG. 6E). Both injection intratumorally and intraperitoneally with TAT-GBRL2 peptide significantly reduced tumor growth in vivo (FIG. 6F). Taken together, these results indicated that TAT-GBRL2 peptide might be potent as an ATG4 inhibitor and tumor repression.

Discussion

ATG4 is a cysteine protease required for autophagy and normal physiology. Nevertheless, overexpression of ATG4 is highly associated with cancer proliferation and malignancy. RNAi and small molecule inhibitors of ATG4 also demonstrate antitumor effects in various cancer cells. However, little is known about the effects of peptide on ATG4 and cancer. Herein, the findings were as follows. First, α-helical peptides derived from ATG8 mammalian homologues inhibited ATG4 proteolytic activity, particularly in H2 peptide derived from GBRL2 and MAP1LC3B. Second, the GBRL2 peptide fusion with TAT1 significantly inhibited cellular ATG4 and autophagic flux. Third, TAT-GBRL2 peptide had stronger inhibition on cancer cell viability and metastatic characteristics compared to GBRL2 peptide. Fourth, TAT-GBRL2 peptide diminished the tumorsphere formation and tumor growth in xenografted mouse. Thus, those results might provide a new TAT-GBRL2 peptide derived from GBRL2 as ATG4 inhibitor and anticancer agent.

Autophagy plays an important role in many diseases, particularly in cancer development. Growing reports have shown that autophagy contributes to cancer malignancy and stemness. For example: I) large-scale screening results of gene mutation for numerous cancer types indicate that autophagy-related (ATG) genes expression are unchanged and non-mutated in most of cancer types, implying ATG genes are active in cancer cells; II) high throughput screening with human shRNA library reveals that ATG4A is required for tumor spheroid formation; III) BECN1, mammalian homologue of ATG6, facilitates CSCs survival and tumor formation in xenografted mouse model; IV) autophagy deficiency decreases osteosarcoma CSCs and results in elevated chemosensitivity; V) ATG7-deficiency activates T-cell activation for tumor suppression of colorectal cancer; VI) systemic knockout of ATG7 has greater suppression on tumor formation of Kras-driven cancer cells compared to ATG7 knockout in only tumor cells, suggesting that autophagy may not only promote tumor cell survival, but also facilitate tumor microenvironments. Those results may provide a novel autophagy inhibitory peptide for cancer suppression.

In summary, specific peptide, specific dosages, specific treatments, specific analysis models or specific evaluating methods are exemplified for clarifying the isolated peptide, the anti-cancer medicinal composition including the same and the method of specifically reducing or inhibiting activities of cancer cells using the same. However, as is understood by a person skilled in the art, other peptides similar to TAT-GBRL2 peptide, other dosages, other treatments, other analysis models or other evaluating methods can be also adopted in the isolated peptide, the anti-cancer medicinal composition including the same and the method of specifically reducing or inhibiting activities of cancer cells using the same without departing the spirit and scope of the present invention rather than being limited as aforementioned.

According to the embodiments of the present invention, the isolated peptide, the anti-cancer medicinal composition including the same and the method of specifically reducing or inhibiting activities of cancer cells using the same, the TAT-GBRL2 peptide can be administered to a subject with a cancer, leading in specifically reducing or inhibiting the function and activities of cancer cells.

Although the present invention has been described in considerable detail with reference to certain embodiments thereof, other embodiments are possible. Therefore, the spirit and scope of the appended claims should not be limited to the description of the embodiments contained herein.

REFERENCE

Dikic I, Elazar Z. Mechanism and medical implications of mammalian autophagy. Nat Rev Mol Cell Biol. 2018; 19(6):349-364.

Mizushima N, Levine B, Cuervo A M, Klionsky D J. Autophagy fights disease through cellular self-digestion. Nature. 2008; 451(7182):1069-1075.

Liu P F, Leung C M, Chang Y H, et al. ATG4B promotes colorectal cancer growth independent of autophagic flux. Autophagy. 2014; 10(8):1454-1465.

Liu P F, Chen H C, Cheng J S, et al. Association of ATG4B and Phosphorylated ATG4B Proteins with Tumorigenesis and Prognosis in Oral Squamous Cell Carcinoma. Cancers (Basel). 2019; 11(12).

Rothe K, Lin H, Lin K B, et al. The core autophagy protein ATG4B is a potential biomarker and therapeutic target in CML stem/progenitor cells. Blood. 2014; 123(23):3622-3634.

Maruyama T, Noda N N. Autophagy-regulating protease Atg4: structure, function, regulation and inhibition. J Antibiot (Tokyo). 2017.

Akin D, Wang S K, Habibzadegah-Tari P, et al. A novel ATG4B antagonist inhibits autophagy and has a negative impact on osteosarcoma tumors. Autophagy. 2014; 10(11):2021-2035.

Liu P F, Hsu C J, Tsai W L, et al. Ablation of ATG4B Suppressed Autophagy and Activated AMPK for Cell Cycle Arrest in Cancer Cells. Cell Physiol Biochem. 2017; 44(2):728-740.

Mao J J, Wu L X, Wang W, et al. Nucleotide variation in ATG4A and susceptibility to cervical cancer in Southwestern Chinese women. Oncol Lett. 2018; 15(3): 2992-3000.

Wolf J, Dewi D L, Fredebohm J, et al. A mammosphere formation RNAi screen reveals that ATG4A promotes a breast cancer stem-like phenotype. Breast Cancer Res. 2013; 15(6): R109.

Antonelli M, Strappazzon F, Arisi I, et al. ATM kinase sustains breast cancer stem-like cells by promoting ATG4C expression and autophagy. Oncotarget. 2017; 8(13):21692-21709.

Read R, Savelieva K, Baker K, Hansen G, Vogel P. Histopathological and neurological features of Atg4b knockout mice. Vet Pathol. 2011; 48(2):486-494.

Marino G, Fernandez A F, Cabrera S, et al. Autophagy is essential for mouse sense of balance. J Clin Invest. 2010; 120(7):2331-2344.

Liu P F, Tsai K L, Hsu C J, et al. Drug Repurposing Screening Identifies Tioconazole as an ATG4 Inhibitor that Suppresses Autophagy and Sensitizes Cancer Cells to Chemotherapy. Theranostics. 2018; 8(3):830-845.

Chang H W, Liu P F, Tsai W L, et al. *Xanthium strumarium* Fruit Extract Inhibits ATG4B and Diminishes the Proliferation and Metastatic Characteristics of Colorectal Cancer Cells. Toxins (Basel). 2019; 11(6).

Mathew R, Karp C M, Beaudoin B, et al. Autophagy suppresses tumorigenesis through elimination of p62. Cell. 2009; 137(6):1062-1075.

Mizushima N, Yoshimori T, Levine B. Methods in mammalian autophagy research. Cell. 2010; 140(3):313-326.

Sanjiv K, Su T L, Suman S, et al. The novel DNA alkylating agent BO-1090 suppresses the growth of human oral cavity cancer in xenografted and orthotopic mouse models. Int J Cancer. 2012; 130(6):1440-1450.

Lebovitz C B, Robertson A G, Goya R, et al. Cross-cancer profiling of molecular alterations within the human autophagy interaction network. Autophagy. 2015; 11(9):1668-1687.

What is claimed is:

1. A method of specifically reducing or inhibiting activities of a cancer, comprising:
   administering a pharmaceutically effective dose of an isolated peptide of SEQ ID NO: 10 to a subject in need thereof.

2. A method of specifically reducing or inhibiting activities of cancer cells, comprising:
   administering a pharmaceutically effective dose of an isolated peptide of SEQ ID NO: 10 to the cancer cells in need thereof.

3. The method of claim 2, wherein a type of the cancer cells is selected from the group consisting of colorectal cancer, glioblastoma, oral cancer, hepatocellular carcinoma, breast cancer, prostate cancer and lung cancer.

4. The method of claim 2, wherein the activities of the cancer cells is selected from the group consisting of ATG4 proteolytic activity, cell migration, invasion and stemness.

* * * * *

SEQUENCE LISTING

```
<160> NUMBER OF SEQ ID NOS: 18

<210> SEQ ID NO 1
<211> LENGTH: 11
<212> TYPE: PRT
<213> ORGANISM: Artificial sequence
<220> FEATURE:
<223> OTHER INFORMATION: GABARAPL2 H2 domain

<400> SEQUENCE: 1

Val Ala Gln Phe Met Trp Ile Ile Arg Lys Arg
                 5                  10

<210> SEQ ID NO 2
<211> LENGTH: 11
```

```
<212> TYPE: PRT
<213> ORGANISM: Artificial sequence
<220> FEATURE:
<223> OTHER INFORMATION: HIV-1 TAT basic domain

<400> SEQUENCE: 2

Tyr Gly Arg Lys Lys Arg Arg Gln Arg Arg
                5                   10

<210> SEQ ID NO 3
<211> LENGTH: 3
<212> TYPE: PRT
<213> ORGANISM: Artificial sequence
<220> FEATURE:
<223> OTHER INFORMATION: peptide linker

<400> SEQUENCE: 3

Gly Gly Ser

<210> SEQ ID NO 4
<211> LENGTH: 3
<212> TYPE: PRT
<213> ORGANISM: Artificial sequence
<220> FEATURE:
<223> OTHER INFORMATION: peptide linker

<400> SEQUENCE: 4

Gly Gly Gly

<210> SEQ ID NO 5
<211> LENGTH: 4
<212> TYPE: PRT
<213> ORGANISM: Artificial sequence
<220> FEATURE:
<223> OTHER INFORMATION: peptide linker

<400> SEQUENCE: 5

Gly Gly Gly Ser

<210> SEQ ID NO 6
<211> LENGTH: 4
<212> TYPE: PRT
<213> ORGANISM: Artificial sequence
<220> FEATURE:
<223> OTHER INFORMATION: peptide linker

<400> SEQUENCE: 6

Gly Gly Gly Gly

<210> SEQ ID NO 7
<211> LENGTH: 5
<212> TYPE: PRT
<213> ORGANISM: Artificial sequence
<220> FEATURE:
<223> OTHER INFORMATION: peptide linker

<400> SEQUENCE: 7

Gly Gly Gly Gly Ser
                5

<210> SEQ ID NO 8
<211> LENGTH: 5
<212> TYPE: PRT
<213> ORGANISM: Artificial sequence
<220> FEATURE:
<223> OTHER INFORMATION: peptide linker
```

```
<400> SEQUENCE: 8

Gly Gly Gly Gly Gly
              5

<210> SEQ ID NO 9
<211> LENGTH: 5
<212> TYPE: PRT
<213> ORGANISM: Artificial sequence
<220> FEATURE:
<223> OTHER INFORMATION: peptide linker

<400> SEQUENCE: 9

Gly Gly Ala Gly Gly
              5

<210> SEQ ID NO 10
<211> LENGTH: 25
<212> TYPE: PRT
<213> ORGANISM: Artificial sequence
<220> FEATURE:
<223> OTHER INFORMATION: TAT-GBL2 peptide

<400> SEQUENCE: 10

Tyr Gly Arg Lys Lys Arg Arg Gln Arg Arg Gly Gly Ser Val Ala
              5                  10                  15

Gln Phe Met Trp Ile Ile Arg Lys Arg
             20                  25

<210> SEQ ID NO 11
<211> LENGTH: 14
<212> TYPE: PRT
<213> ORGANISM: Artificial sequence
<220> FEATURE:
<223> OTHER INFORMATION: GABARAPL2 H1 domain

<400> SEQUENCE: 11

Leu Glu His Arg Cys Val Glu Ser Ala Lys Ile Arg Ala Lys
              5                  10

<210> SEQ ID NO 12
<211> LENGTH: 8
<212> TYPE: PRT
<213> ORGANISM: Artificial sequence
<220> FEATURE:
<223> OTHER INFORMATION: GABARAPL2 H3 domain

<400> SEQUENCE: 12

Met Gly Gln Leu Tyr Glu Lys Glu
              5

<210> SEQ ID NO 13
<211> LENGTH: 117
<212> TYPE: PRT
<213> ORGANISM: Artificial sequence
<220> FEATURE:
<223> OTHER INFORMATION: Human GBRL2

<400> SEQUENCE: 13

Met Lys Trp Met Phe Lys Glu Asp His Ser Leu Glu His Arg Cys Val
              5                  10                  15

Glu Ser Ala Lys Ile Arg Ala Lys Tyr Pro Asp Arg Val Pro Val Ile
             20                  25                  30

Val Glu Lys Val Ser Gly Ser Gln Ile Val Asp Ile Asp Lys Arg Lys
         35                  40                  45
```

```
Tyr Leu Val Pro Ser Asp Ile Thr Val Ala Gln Phe Met Trp Ile Ile
    50                  55                  60
Arg Lys Arg Ile Gln Leu Pro Ser Glu Lys Ala Ile Phe Leu Phe Val
65                  70                  75                  80
Asp Lys Thr Val Pro Gln Ser Ser Leu Thr Met Gly Gln Leu Tyr Glu
                85                  90                  95
Lys Glu Lys Asp Glu Asp Gly Phe Leu Tyr Val Ala Tyr Ser Gly Glu
                100                 105                 110
Asn Thr Phe Gly Phe
            115
```

<210> SEQ ID NO 14
<211> LENGTH: 117
<212> TYPE: PRT
<213> ORGANISM: Artificial sequence
<220> FEATURE:
<223> OTHER INFORMATION: Human GBRAP

<400> SEQUENCE: 14

```
Met Lys Phe Val Tyr Lys Glu Glu His Pro Phe Glu Lys Arg Arg Ser
                5                   10                  15
Glu Gly Glu Lys Ile Arg Lys Lys Tyr Pro Asp Arg Val Pro Val Ile
                20                  25                  30
Val Glu Lys Ala Pro Lys Ala Arg Ile Gly Asp Leu Asp Lys Lys Lys
                35                  40                  45
Tyr Leu Val Pro Ser Asp Leu Thr Val Gly Gln Phe Tyr Phe Leu Ile
    50                  55                  60
Arg Lys Arg Ile His Leu Arg Ala Glu Asp Ala Leu Phe Phe Phe Val
65                  70                  75                  80
Asn Asn Val Ile Pro Pro Thr Ser Ala Thr Met Gly Gln Leu Tyr Gln
                85                  90                  95
Glu His His Glu Glu Asp Phe Phe Leu Tyr Ile Ala Tyr Ser Asp Glu
                100                 105                 110
Ser Val Tyr Gly Leu
            115
```

<210> SEQ ID NO 15
<211> LENGTH: 117
<212> TYPE: PRT
<213> ORGANISM: Artificial sequence
<220> FEATURE:
<223> OTHER INFORMATION: Human GBRL1

<400> SEQUENCE: 15

```
Met Lys Phe Gln Tyr Lys Glu Asp His Pro Phe Glu Tyr Arg Lys Lys
                5                   10                  15
Glu Gly Glu Lys Ile Arg Lys Lys Tyr Pro Asp Arg Val Pro Val Ile
                20                  25                  30
Val Glu Lys Ala Pro Lys Ala Arg Val Pro Asp Leu Asp Lys Arg Lys
                35                  40                  45
Tyr Leu Val Pro Ser Asp Leu Thr Val Gly Gln Phe Tyr Phe Leu Ile
    50                  55                  60
Arg Lys Arg Ile His Leu Arg Pro Glu Asp Ala Leu Phe Phe Phe Val
65                  70                  75                  80
Asn Asn Thr Ile Pro Pro Thr Ser Ala Thr Met Gly Gln Leu Tyr Glu
                85                  90                  95
Asp Asn His Glu Glu Asp Tyr Phe Leu Tyr Val Ala Tyr Ser Asp Glu
                100                 105                 110
```

```
Ser Val Tyr Gly Lys
        115

<210> SEQ ID NO 16
<211> LENGTH: 147
<212> TYPE: PRT
<213> ORGANISM: Artificial sequence
<220> FEATURE:
<223> OTHER INFORMATION: Human MLP3C

<400> SEQUENCE: 16

Met Pro Pro Gln Lys Ile Pro Ser Val Arg Pro Phe Lys Gln Arg
                5                  10                 15

Lys Ser Leu Ala Ile Arg Gln Glu Glu Val Ala Gly Ile Arg Ala Lys
            20                  25                  30

Phe Pro Asn Lys Ile Pro Val Val Val Glu Arg Tyr Pro Arg Glu Thr
            35                  40                  45

Phe Leu Pro Pro Leu Asp Lys Thr Lys Tyr Leu Val Pro Gln Glu Leu
        50                  55                  60

Thr Met Thr Gln Phe Leu Ser Ile Ile Arg Ser Arg Met Val Leu Arg
65                  70                  75                  80

Ala Thr Glu Ala Phe Tyr Leu Leu Val Asn Asn Lys Ser Leu Val Ser
                85                  90                  95

Met Ser Ala Thr Met Ala Glu Ile Tyr Arg Asp Tyr Lys Asp Glu Asp
            100                 105                 110

Gly Phe Val Tyr Met Thr Tyr Ala Ser Gln Glu Thr Phe Gly Cys Leu
            115                 120                 125

Glu Ser Ala Ala Pro Arg Asp Gly Ser Ser Leu Glu Asp Arg Pro Cys
        130                 135                 140

Asn Pro Leu
145

<210> SEQ ID NO 17
<211> LENGTH: 121
<212> TYPE: PRT
<213> ORGANISM: Artificial sequence
<220> FEATURE:
<223> OTHER INFORMATION: Human MLP3A

<400> SEQUENCE: 17

Met Pro Ser Asp Arg Pro Phe Lys Gln Arg Arg Ser Phe Ala Asp Arg
                5                  10                 15

Cys Lys Glu Val Gln Gln Ile Arg Asp Gln His Pro Ser Lys Ile Pro
            20                  25                  30

Val Ile Ile Glu Arg Tyr Lys Gly Glu Lys Gln Leu Pro Val Leu Asp
            35                  40                  45

Lys Thr Lys Phe Leu Val Pro Asp His Val Asn Met Ser Glu Leu Val
        50                  55                  60

Lys Ile Ile Arg Arg Arg Leu Gln Leu Asn Pro Thr Gln Ala Phe Phe
65                  70                  75                  80

Leu Leu Val Asn Gln His Ser Met Val Ser Val Ser Thr Pro Ile Ala
                85                  90                  95

Asp Ile Tyr Glu Gln Glu Lys Asp Glu Asp Gly Phe Leu Tyr Met Val
            100                 105                 110

Tyr Ala Ser Gln Glu Thr Phe Gly Phe
            115                 120
```

```
<210> SEQ ID NO 18
<211> LENGTH: 125
<212> TYPE: PRT
<213> ORGANISM: Artificial sequence
<220> FEATURE:
<223> OTHER INFORMATION: Human MLP3B

<400> SEQUENCE: 18

Met Pro Ser Glu Lys Thr Phe Lys Gln Arg Arg Thr Phe Glu Gln Arg
                 5                  10                  15

Val Glu Asp Val Arg Leu Ile Arg Glu Gln His Pro Thr Lys Ile Pro
             20                  25                  30

Val Ile Ile Glu Arg Tyr Lys Gly Glu Lys Gln Leu Pro Val Leu Asp
         35                  40                  45

Lys Thr Lys Phe Leu Val Pro Asp His Val Asn Met Ser Glu Leu Ile
     50                  55                  60

Lys Ile Ile Arg Arg Arg Leu Gln Leu Asn Ala Thr Gln Ala Phe Phe
 65                  70                  75                  80

Leu Leu Val Asn Gly His Ser Met Val Ser Val Ser Thr Pro Ile Ser
                 85                  90                  95

Glu Val Tyr Glu Ser Glu Lys Asp Glu Asp Gly Phe Leu Tyr Met Val
            100                 105                 110

Tyr Ala Ser Gln Glu Thr Phe Gly Met Lys Leu Ser Val
        115                 120                 125
```